(12) United States Patent
Ford et al.

(10) Patent No.: US 8,411,262 B2
(45) Date of Patent: Apr. 2, 2013

(54) DOWNHOLE GAS BREAKOUT SENSOR

(75) Inventors: Jess V. Ford, Weatherford, TX (US); Sean M. Christian, Land O Lakes, FL (US); Bryan W. Kasperski, Carrollton, TX (US); Tom Haslett, Toronto (CA); Dave Demmer, Toronto (CA); Margaret C. Waid, Aledo, TX (US); Mike Yuratich, Hamble Hants (GB)

(73) Assignee: Precision Energy Services, Inc., Fort Worth, TX (US)

( * ) Notice: Subject to any disclaimer, the term of this patent is extended or adjusted under 35 U.S.C. 154(b) by 0 days.

(21) Appl. No.: 12/894,342

(22) Filed: Sep. 30, 2010

(65) Prior Publication Data

US 2012/0081699 A1 Apr. 5, 2012

(51) Int. Cl.
*G01N 21/41* (2006.01)
(52) U.S. Cl. ........................................ 356/128
(58) Field of Classification Search .................. None
See application file for complete search history.

(56) References Cited

U.S. PATENT DOCUMENTS

| | | |
|---|---|---|
| 2,807,976 A | 10/1957 | Vossberg |
| 3,628,867 A | 12/1971 | Brady |
| 3,999,857 A | 12/1976 | David et al. |
| 4,264,205 A | 4/1981 | Landa |
| 4,285,596 A | 8/1981 | Landa |
| 4,569,590 A | 2/1986 | Karney et al. |
| 4,571,082 A | 2/1986 | Downs |
| 4,632,528 A | 12/1986 | Yoshino et al. |
| 4,682,889 A | 7/1987 | Harmer |
| 4,692,024 A | 9/1987 | Bloss |
| 4,785,806 A | 11/1988 | Deckelbaum |
| 4,832,490 A | 5/1989 | Boos |
| 4,834,533 A | 5/1989 | Horike et al. |

(Continued)

FOREIGN PATENT DOCUMENTS

| | | |
|---|---|---|
| EP | 0341927 A1 | 11/1989 |
| GB | 2391939 A | 2/2004 |

(Continued)

OTHER PUBLICATIONS

Cantrell, "The SLIM Spectrometer" Anal. Chem. 2003, 75, pp. 27-35, Department of Chemistry, Oregon State University, 153 Gilbert Hall, Corvallis, Oregon 97331-4001.

(Continued)

*Primary Examiner* — Gregory J Toatley
*Assistant Examiner* — Amanda Merlino
(74) *Attorney, Agent, or Firm* — Wong, Cabello, Lutsch, Rutherford & Brucculeri, L.L.P.

(57) ABSTRACT

A downhole fluid analysis tool has a housing and a flow passage for downhole fluid. A device disposed in the tool housing relative to the flow passage has a one or more sources, one or more sensing optics, one or more detectors, and control circuitry. The source generates an input signal. The sensing optic has a refractive index (RI) higher than crude oil and other expected constituents. A sensing surface of the optic optically coupled to the source interfaces with a downhole fluid. When the variable RI of the downhole fluid reaches a defined relationship to the optic's RI, the input signal interacting with the sensing surface experiences total internal reflection, and the reflected signal from the sensing surface remains in the sensing optic and reflects to a detector. The control circuitry monitors the detector's response and indicates gas break out if the response is above a threshold.

55 Claims, 7 Drawing Sheets

U.S. PATENT DOCUMENTS

| | | | |
|---|---|---|---|
| 4,929,049 A | 5/1990 | Le Goullon et al. |
| 4,952,055 A | 8/1990 | Wyatt |
| 4,962,815 A | 10/1990 | Schultz et al. |
| 4,968,148 A | 11/1990 | Chow |
| 4,994,671 A | 2/1991 | Safinya et al. |
| 5,026,139 A | 6/1991 | Klainer et al. |
| 5,083,018 A | 1/1992 | Rhyne |
| 5,128,797 A | 7/1992 | Sachse et al. |
| 5,139,661 A | 8/1992 | Kolbert |
| 5,166,747 A | 11/1992 | Schroeder et al. |
| 5,167,149 A | 12/1992 | Mullins et al. |
| 5,170,056 A | 12/1992 | Berard |
| 5,201,220 A | 4/1993 | Mullins et al. |
| 5,257,086 A | 10/1993 | Fateley et al. |
| 5,337,621 A | 8/1994 | Spease |
| 5,371,543 A | 12/1994 | Anderson |
| 5,440,118 A | 8/1995 | Roscoe |
| 5,504,575 A | 4/1996 | Stafford |
| 5,565,978 A | 10/1996 | Okubo et al. |
| 5,617,201 A | 4/1997 | Kahre |
| 5,629,125 A | 5/1997 | Leblans et al. |
| 5,633,708 A | 5/1997 | Svendsen |
| 5,663,790 A | 9/1997 | Ekstrom et al. |
| 5,825,478 A | 10/1998 | Wilcox |
| 5,828,066 A | 10/1998 | Messerschmidt |
| 5,859,430 A | 1/1999 | Mullins et al. |
| 5,939,717 A | 8/1999 | Mullins |
| 6,075,595 A | 6/2000 | Malinen |
| 6,128,078 A | 10/2000 | Fateley |
| 6,130,439 A | 10/2000 | Le Menn |
| 6,172,746 B1 | 1/2001 | Byrne et al. |
| 6,274,865 B1 | 8/2001 | Schroer et al. |
| 6,301,959 B1 | 10/2001 | Hrametz et al. |
| 6,350,986 B1 | 2/2002 | Mullins et al. |
| 6,356,675 B1 | 3/2002 | Weiss |
| 6,388,251 B1 | 5/2002 | Papanyan |
| 6,420,695 B1 | 7/2002 | Grasdepot |
| 6,429,936 B1 | 8/2002 | Scaduto |
| 6,437,326 B1 | 8/2002 | Yamate et al. |
| 6,465,775 B2 | 10/2002 | Mullins et al. |
| 6,474,152 B1 | 11/2002 | Mullins et al. |
| 6,476,384 B1 | 11/2002 | Mullins et al. |
| 6,504,943 B1 | 1/2003 | Sweatt et al. |
| 6,559,945 B1 | 5/2003 | Grasdepot |
| 6,571,118 B1 | 5/2003 | Utzinger et al. |
| 6,600,591 B2 | 7/2003 | Anderson et al. |
| 6,678,050 B2 | 1/2004 | Pope et al. |
| 6,683,681 B2 | 1/2004 | DiFoggio et al. |
| 6,693,701 B2 | 2/2004 | Hansen |
| 6,753,960 B1 | 6/2004 | Polynkin et al. |
| 6,758,090 B2 | 7/2004 | Bostrom et al. |
| 6,768,105 B2 | 7/2004 | Mullins et al. |
| 6,781,691 B2 | 8/2004 | MacKinnon et al. |
| 6,798,518 B2 | 9/2004 | DiFoggio et al. |
| 6,870,619 B1 | 3/2005 | Tenhunen et al. |
| 6,939,717 B2 | 9/2005 | Jiang |
| 6,967,714 B2 | 11/2005 | Koops et al. |
| 6,995,360 B2 | 2/2006 | Jones et al. |
| 6,997,055 B2 | 2/2006 | DiFoggio |
| 7,002,142 B2 | 2/2006 | Mullins et al. |
| 7,013,723 B2 | 3/2006 | Ramakrishnan et al. |
| 7,016,026 B2 | 3/2006 | DiFoggio et al. |
| 7,024,060 B2 | 4/2006 | Cardenas-Valencia et al. |
| 7,028,773 B2 | 4/2006 | Fujisawa et al. |
| 7,075,063 B2 | 7/2006 | Dong et al. |
| 7,084,392 B2 | 8/2006 | DiFoggio et al. |
| 7,095,012 B2 | 8/2006 | Fujisawa et al. |
| 7,173,239 B2 | 2/2007 | DiFoggio |
| 7,199,871 B2 | 4/2007 | Frot |
| 7,214,933 B2 | 5/2007 | DiFoggio et al. |
| 7,262,866 B2 | 8/2007 | Ivarsson |
| 7,265,830 B2 | 9/2007 | Wang |
| 7,279,678 B2 | 10/2007 | Andrews et al. |
| 7,280,214 B2 | 10/2007 | DiFoggio et al. |
| 7,299,136 B2 | 11/2007 | DiFoggio et al. |
| 7,321,428 B2 | 1/2008 | Hunt |
| 7,336,356 B2 | 2/2008 | Vannuffelen et al. |
| 7,360,924 B2 | 4/2008 | Henson et al. |
| 7,362,422 B2 | 4/2008 | DiFoggio et al. |
| 7,379,180 B2 | 5/2008 | Vannuffelen et al. |
| 7,392,697 B2 | 7/2008 | Chikenji et al. |
| 7,403,680 B2 | 7/2008 | Simbal |
| 7,440,098 B2 | 10/2008 | Christian et al. |
| 7,445,043 B2 | 11/2008 | Mullins et al. |
| 7,461,547 B2 | 12/2008 | Terabayashi et al. |
| 7,475,593 B2 | 1/2009 | Odom |
| 7,508,506 B2 | 3/2009 | Christian et al. |
| 7,511,813 B2 | 3/2009 | Vannuffelen et al. |
| 7,526,953 B2 | 5/2009 | Goodwin et al. |
| 7,609,380 B2 | 10/2009 | Vannuffelen et al. |
| 2003/0206026 A1 | 11/2003 | Diakonov et al. |
| 2003/0223068 A1 | 12/2003 | DiFoggio et al. |
| 2004/0169858 A1 | 9/2004 | Da Silva |
| 2004/0201850 A1 | 10/2004 | Hajian et al. |
| 2004/0239923 A1 | 12/2004 | Adams et al. |
| 2004/0239931 A1 | 12/2004 | Teichmann et al. |
| 2004/0253735 A1 | 12/2004 | Vadgama et al. |
| 2005/0185179 A1 | 8/2005 | Wang |
| 2005/0243312 A1 | 11/2005 | Geshwind et al. |
| 2005/0262936 A1 | 12/2005 | DiFoggio |
| 2005/0269499 A1 | 12/2005 | Jones et al. |
| 2006/0241866 A1 | 10/2006 | DiFoggio |
| 2006/0243033 A1 | 11/2006 | Freemark et al. |
| 2007/0013911 A1 | 1/2007 | DiFoggio |
| 2007/0109537 A1 | 5/2007 | Vannuffelen |
| 2007/0159625 A1 | 7/2007 | DiFoggio |
| 2007/0171412 A1 | 7/2007 | Vannuffelen |
| 2007/0171414 A1 | 7/2007 | Vannuffelen |
| 2007/0229821 A1 | 10/2007 | Christian et al. |
| 2007/0238180 A1 | 10/2007 | DiFoggio et al. |
| 2008/0030739 A1 | 2/2008 | Hartog et al. |
| 2008/0078544 A1 | 4/2008 | Christian et al. |
| 2008/0087078 A1 | 4/2008 | Vannuffelen |
| 2008/0165356 A1 | 7/2008 | Difoggio et al. |
| 2008/0173083 A1 | 7/2008 | Kasperski et al. |
| 2008/0173804 A1 | 7/2008 | Indo et al. |
| 2008/0173805 A1 | 7/2008 | Indo et al. |
| 2008/0174777 A1 | 7/2008 | Carron |
| 2008/0314138 A1 | 12/2008 | Brady |
| 2009/0059332 A1 | 3/2009 | DiFoggio et al. |
| 2009/0166085 A1 | 7/2009 | Ciglenec et al. |
| 2010/0015612 A1* | 1/2010 | Pelham et al. ............... 435/6 |
| 2010/0025112 A1 | 2/2010 | Sroka et al. |
| 2010/0205139 A1* | 8/2010 | Xia et al. ............... 706/54 |

FOREIGN PATENT DOCUMENTS

| | | |
|---|---|---|
| JP | 61-011636 | 1/1986 |
| WO | 81/00775 | 3/1981 |
| WO | 95/04263 | 2/1995 |

OTHER PUBLICATIONS

Hauser, "A Multi-Wavelength Photometer Based on Light-Emitting Diodes" Talanta, vol. 42, No. 4, pp. 605-612, 1995.

Keranen, "Analytic and Raytrace Modeling of a Miniaturized Infrared Spectrometer Module".

Malinen et al., Sensors and Actuators B 51 (1998) 220-224,"LED-based NIR spectrometer available module for hand-held and process analyser applications," dated Jun. 16, 1998.

O'Toole, "Absorbance Based Light Emitting Diode Optical Sensors and Sensing Devices," Sensors 2008, 8, pp. 2453-2479; dated Apr. 7, 2008 obtained from www.mdpi.org/sensors.

Palma, "Portable light-emitting diode-based photometer with one-shot optochemical sensors for measurement in the field," dated Oct. 21, 2008, American Institute of Physics.

Schlumberger, "Fundamentals of Formation Testing," © 2006, pp. 1-5, 27-29, 55-67, 99-124, 199-202, Schlumberger Marketing Communications, Sugar Land, Texas, United States.

Schlumberger, "Engineering the Next-Generation Downhole Fluid Analysis Tool," dated May 7, 2007.

OZ Optics, "Silicon Optical Bench Platforms," dated Nov. 14, 2002, obtained from www.ozoptics.com.

Yeh, "A Low Cost LED Based Spectrometer," Journal of the Chinese Chemical Society, 2006, 53, pp. 1067-1072.

Thorlabs Inc., "Stepped Circular Neutral Density Filter," Drawing No. 10661-E01, Part No. NDC-100S-4.

Thorlabs Inc., "Mounted Round Step Variable NDC Filter," Drawing No. 10664-E01, Part No. NDC-100S-4M.

Frentress, "Field Photometer with Nine-Element Filter Wheel," dated Feb. 1964, vol. 3, No. 2, Applied Optics, pp. 303-308.

International Search Report and Written Opinion in corresponding Application No. PCT/US07/82221, dated May 5, 2008.

International Search Report, International Patent Application No. PCT/US07/080112, mailed on Mar. 25, 2008.

Dudley, Dana, et al., "Emerging Digital Micromirror Device (DMD) Applications," DLP Products New Applications, Texas Instruments, Inc. undated.

Wagner, Eugene P. II, et al., "Construction and Evaluation of a Visible Spectrometer Using Digital Micromirror Spatial Light Modulation," Applied Spectroscopy, vol. 49, No. 11, 1995.

Ford, Joseph E., et al., "Dynamic Spectral Power Equalization Using Micro-Opto-Mechanics," IEEE Photonics Technology Letters, vol. 10, No. 10, Oct. 1998.

Duncan, Walter M., "Dynamic Optical Filtering in DWDM Systems Using the DMD," Solid State Electronics 46 (2002), pp. 1583-1585.

Lerner, J.M., et al., "The Optics of Spectroscopy—A Tutorial," Instruments SA, Inc., 1988.

Spudich, Thomas M., et al., "Potential for using a Digital Micromirror Device as a Signal Multiplexer in Visible Spectrscopy," Applied Spectroscopy, vol. 57, No. 7, 2003.

DeVerse, R. A., et al, "Realization of the Hadamard Multiplex Advantage Using a Programmable Optical Mask in a Dispersive Flat-Field Near-Infrared Spectrometer," Applied Spectroscopy, vol. 54, No. 12, 2000.

Badry, R., et al., "Downhole Optical Analysis of Formation Fluids," Oilfield Review, Jan. 1994.

Schroeder, R., "Slick Engineering," Spie's OE Magazine, May 2003.

Raghuraman, B., "Real-Time Downhold pH Measurement Using Optical Spectroscopy," SPE 93057, Society of Petroleum Engineers, 2005.

Sirkis, J., "Multifunctionality The Key in Challenging Instrumentation Markets," Lightwave Magazine, Mar. 2003.

Meyer, R., "RITMOS: A Micromirror-Based Multi-Object Spectrometer," Proceedings of the SPIE, 2004.

Smits, A.R., "In-Situ Optical Fluid Analysis as an Aid to Wireline Formation Sampling," SPE Formation Evaluation, Jun. 1995.

Texas Instruments, Application Report, "Single Panel DLP Projection System Optics," Mar. 2005.

Texas Instruments, Product Preview, "DMD 0.7 XGA 12.degree. LVDS DMD Discovery," Jul. 2005.

Texas Instruments, Product Preview Data Sheet, "DMD 0.7 XGA 12.degree. DDR DMD Discovery," Aug. 30, 2005.

Texas Instruments, "DMD Discovery 1100 Chip Set," 2004.

Texas Instruments, "DMD Discovery 3000 Digital Controller (DDC3000) Starter Kit Technical Reference Manual," Oct. 2005.

Texas Instruments, "DMD Discovery 1100 Controller Board and Starter Kit," Oct. 2004.

Baker Hughes, "RCI Reservoir Characterization Instrument," obtained from www.bakerhughesdirect.com, generated on Apr. 8, 2010.

Baker Hughes, "SampleView" 2000, obtained Apr. 19, 2010 from www.bakerhughesdirect.com, generated on Apr. 19, 2010.

Co-pending U.S. Appl. No. 12/613,808, entitled "Multi-Channel Detector Assembly for Downhole Spectroscopy," filed Nov. 6, 2009.

Co-pending U.S. Appl. No. 12/613,700, entitled "Multi-Channel Detector Assembly for Downhole Spectroscopy," filed Nov. 6, 2009.

Co-pending U.S. Appl. No. 12/613,665, entitled "Filter Wheel Assembly for Downhole Spectroscopy," filed Nov. 6, 2009.

First Examination Report in counterpart Australian Appl. 2011224006, dated Jul. 13, 2012.

English Abstract of JP 61-011636, obtained from Japanese Patent Office, Jan. 20, 1986.

Search Report in counterpart European Appl. 11181777.1, dated Sep. 11, 2012.

Search Report in counterpart Australian Appl. 2011224005, dated Oct. 29, 2012.

* cited by examiner

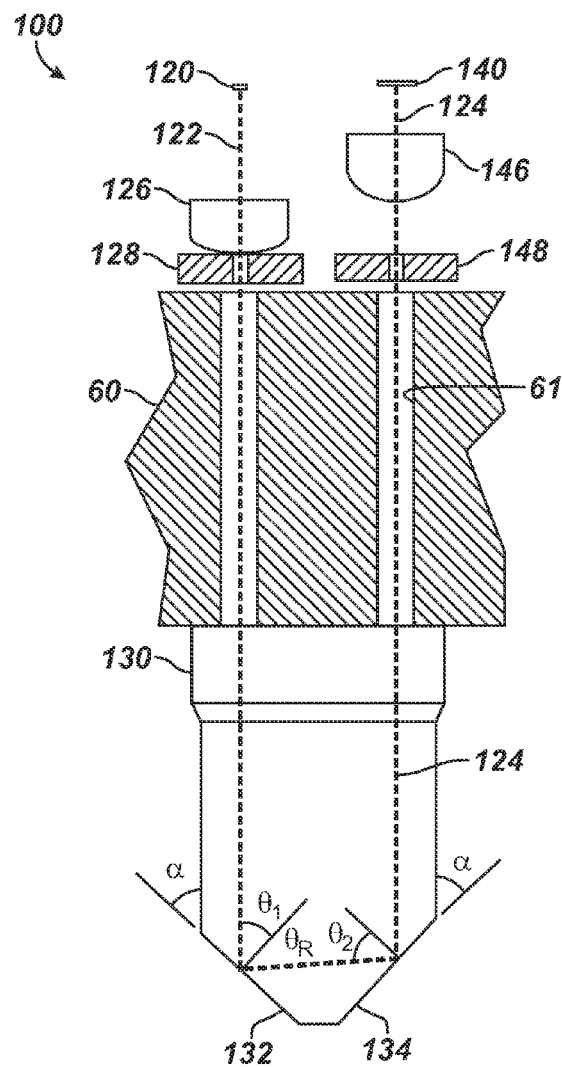
FIG. 6
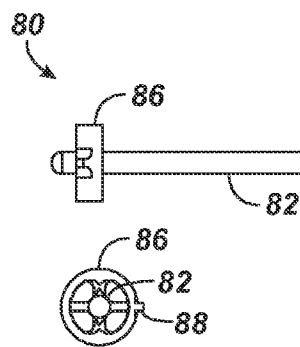
FIG. 8A
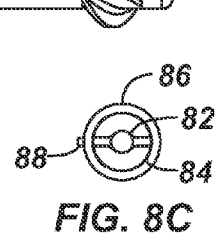
FIG. 8B
FIG. 8C

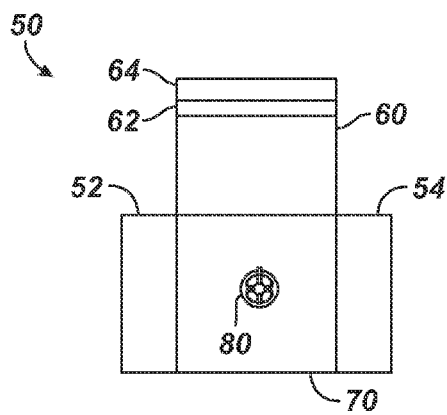
FIG. 7B
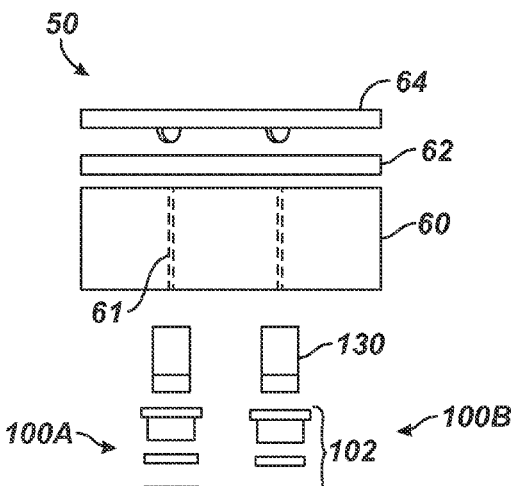
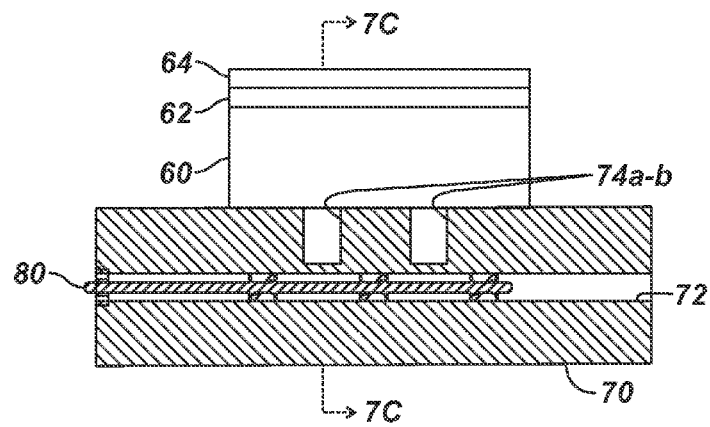
FIG. 7A
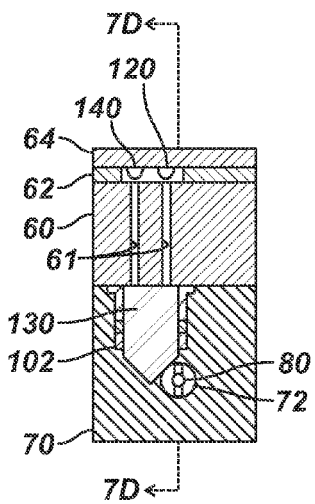
FIG. 7C
FIG. 7D

DOWNHOLE GAS BREAKOUT SENSOR

CROSS-REFERENCE TO RELATED APPLICATIONS

This application is filed concurrently with U.S. patent application Ser. No. 12/894,342 and entitled "Refractive Index Sensor for Fluid Analysis," which is incorporated herein by reference in its entirety.

BACKGROUND

Various chemical and physical parameters of a material may be of interest in fluid analysis, process monitoring, and other operations, and a variety of systems can be used to determine such parameters. For example, the index of refraction of a transparent medium may be a parameter of interest in a given operation. A critical angle measurement is one approach that can be used to obtain the index of refraction of an unknown medium.

FIG. 1 helps illustrate index of refraction, critical angle, and other related details. As shown, light rays $R_1$, $R_2$, & $R_3$ pass at different angles through a first (known) transparent medium $M_1$ having a known refractive index $n_1$. The light rays meet the boundary or interface between this medium $M_1$ and a second (unknown) transparent medium $M_2$. In this example, this second medium $M_2$ has an unknown index of refraction $n_2$ that is at least less than the known refractive index $n_1$.

A first light ray $R_1$ passing through the first medium $M_1$ at some angle of incidence (i.e., $\theta_i$) toward the interface will have a portion that passes through the interface and refracts in the second medium $M_2$. This first ray $R_1$ will also have another portion that reflects off the interface back into the same medium $M_1$. At one particular angle of incidence called the critical angle $\theta_{crit}$, however, an incident light ray $R_2$ refracts parallel to the interface (i.e., an angle of 90-degrees relative to the normal of the interface) so that the refracted light passes along the boundary between the mediums $M_1$ & $M_2$. Light rays $R_3$ incident at other angles $\theta_{TIR}$ beyond this critical angle $\theta_{crit}$ will be reflected entirely in the first medium $M_1$. This is referred to as Total Internal Reflection (TIR).

The actual value of the critical angle $\theta_{crit}$ depends on the refractive index of the two mediums $M_1$ & $M_2$. However, direct measurement can be used to find the critical angle $\theta_{crit}$, and Snell's Law can be used to determine the unknown index of refraction of the second medium $M_2$. Snell's Law is characterized as:

$$\frac{\sin\theta_1}{\sin\theta_2} = \frac{v_1}{v_2} = \frac{n_2}{n_1},$$

where
$\theta_1 \equiv$ angle of incidence
$\theta_2 \equiv$ angle of refraction
$v_1 \equiv$ light velocity in material 1
$v_2 \equiv$ light velocity in material 2
$n_1 \equiv$ refractive index or material 1
$n_2 \equiv$ refractive index of material 2
At the critical angle $\theta_{crit}$ when $n_1 > n_2$ (i.e., $$\frac{n_2}{n_1} < 1\bigg),$$

the angle of incidence $\theta_1$ in the equation is the critical angle $\theta_{crit}$, and the angle of refraction $\theta_2$ is 90-degrees relative to the normal of the interface. By determining the critical angle $\theta_{crit}$ between the mediums $M_1$ & $M_2$ and by already knowing the refractive index $n_1$ of the known medium $M_1$, the unknown refractive index $n_2$ of the second medium $M_2$ can be calculated as: $n_2 = n_1 \sin\theta_{crit}$. From this, the refractive index of the second medium $M_2$ can be deduced.

Devices are known in the art that use a critical angle measurement to measure very specific chemical systems, thin films, and the like. One of the most common devices is the Abbe and Pulfrich refractometer. There are also a number of commercially available critical angle based systems for process monitoring and control. In general, all of the above-mentioned systems or classes of systems are not amenable to harsh environments.

There are also other approaches to refractive index measurement, but the operating principles are sufficiently different from the critical angle methodology. As an example, refractive index can be measured by commercially available systems that include Fabry-Perot optical cavities. This type of system is not amenable to harsh environments because of thermal issues with the required electronics and fouling of the measurement region with fluids having viscosities greater than water and/or high particulate loading.

A borehole in a geological formation is an example of a harsh environment where chemical and physical parameters of materials are of interest. Various systems can be conveyed within the borehole during geophysical exploration and production operations to determine the chemical and physical parameters of materials in the borehole environs. These downhole systems can include formation testers and borehole fluid analysis systems that determine parameters of fluids or formation matrix in the vicinity of the borehole as well as materials, such as fluids, within the borehole itself. Preferably, these downhole systems make all measurements in real-time using the available instrumentation in the borehole, although data and fluids can be collected for later retrieval and processing at the surface. In analyzing the fluids, various properties of the fluid may be of interest. For example, the properties include, but are not limited to, fluid density, fluid homogeneity, salinity, gas fraction, asphaltene content, and chemical composition.

One example of such a downhole system is a formation tester tool used in the oil and gas industry to measure pressure, temperature, and other parameters of a formation penetrated by a borehole. The formation tester tool can be conveyed along the borehole, and the tool can collect and analyze fluids from the formation to determine major constituents within the fluid. (By definition, formation fluid is a complex mixture of liquids and/or gases.) Formation tester tools may be deployed on wireline, pipe, or during logging while drilling. Another example is a downhole system for examining fluids in a producing well. The parametric measurements are typically combined with in-situ or uphole analyses of physical and chemical properties of the formation fluid to evaluate production prospects of reservoirs penetrated by the borehole.

When conveyed downhole, the formation tester tool draws fluid into the formation tester tool for pressure measurements, analysis, sampling, and optionally for subsequent exhausting of the fluid into the borehole. Regarding formation fluid sampling, the goal is to collect a single phase formation fluid sample that is representative of the fluids in the formation with minimal contamination from mud system filtrate and/or other drilling fluids.

Regardless of the fluid sampling methodology, the tool may need to maintain certain fluid pressures or other parameters in order to obtain accurate and precise measurements with fluid analysis devices in the tool. Additionally, it is important to know that the fluid being pumped into the tool is fluid that is representative of all of the fluid within the formation and that fluids have not broken out and are being left in the formation. Accordingly, what is needed is a device for a formation tester or other downhole tool that can determine particular parameters of sampled fluid to be analyzed.

SUMMARY

A downhole fluid analysis tool has a tool housing deployable downhole and has a flow passage for downhole fluid. A fluid analysis device is disposed in the tool housing relative to the flow passage. A source in this device generates an input signal that passes to a sensing optic, which can be composed of sapphire, ruby, zircon, cubic zirconium, diamond, garnet, or other material. The sensing optic has a known refractive index selected to be higher than crude oil and other expected constituents of the downhole fluid. A sensing surface of the optic interfaces with the downhole fluid as it flows through the flow passage.

The downhole fluid's refractive index is unknown and may vary depending on its constituents and other variables (i.e., pressure, temperature, etc.) as it is drawn through the flow passage. When the fluid's variable refractive index has a defined relationship to the optic's known refractive index, the input signal interacting with the optic's sensing surface experiences total internal reflection within the sensing optic. When this occurs, a reflected signal from the sensing surface remains in the optic, and a second mirrored surface of the optic reflects the reflected signal to a detector, which detects the signal's intensity. However, alternate configurations without reflective surfaces for optical routing are possible.

Control circuitry of the device monitors the detector's response and indicates a flag condition if the response is above a certain threshold. In general, the flag condition can indicate that gas breakout has occurred in the fluid flow. Gas breakout is indicated at least when the pressure of the downhole fluid falls below a bubble point of the fluid, which is dependent on the formation temperature and fluid composition. Therefore, the flag condition can indicate that the downhole tool drawing the fluid has reduced the fluid's pressure below its bubble point.

When gas breakout occurs, the variable refractive index of the downhole fluid has changed to a point where the input signal experiences total internal reflection in the sensing optic due to the relationship between the refractive indexes of the optic and the fluid. In response to the gas breakout, operation of the downhole tool can be modified to increase the pressure above the bubble point or to keep the pressure below the bubble point, depending on the desired fluid flow characteristics and what parameters of the fluid are being measured by other fluid analysis devices in the tool.

If the fluid analysis device fails to recognize that gas is present, then the device will fail to detect any change in the flow to below the bubble point even if gas bubbles are actually present in the fluid. For this reason, the device preferably includes a bubble director that helps transport any bubbles present in the flow passage to at least one of the sensors for detecting the gas bubbles. Without such a bubble director, the presence of gas bubbles may be missed, and the current reading from the device would be an inaccurate gas flag measurement. As will be appreciated, an inaccurate gas flag measurement can affect subsequent determinations of the reserves available downhole.

The bubble director inserts into the flow stream passing through the device's flow passage. During use, the bubble director directs bubbles in the flow stream to strike the sensors in particular areas that help in detecting the gas bubbles. The bubble director can have a spiral design so that bubbles in the flow are not missed due to gravity or other reasons as they are transported through the flow passage to the sensors. Moreover, the bubble director preferably maintains the flow rate of the fluid from the formation unchanged and preferably avoids trapping and building mud cake in the device's flow passage.

The foregoing summary is not intended to summarize each potential embodiment or every aspect of the present disclosure.

BRIEF DESCRIPTION OF THE DRAWINGS

The manner in which the above recited features and advantages, briefly summarized above, are obtained can be understood in detail by reference to the embodiments illustrated in the appended drawings.

FIG. 6 shows components on the gas breakout sensor in more detail.

FIG. 7A shows an exploded view of a gas breakout assembly for a formation tester tool.

FIG. 7B is an end view of the gas breakout assembly.

FIG. 7C shows a cross-sectional view of the gas breakout assembly.

FIG. 7D is an end-sectional view of the gas breakout assembly.

FIGS. 8A-8C show side and two ends views of a bubble director for the gas breakout assembly.

DETAILED DESCRIPTION

A. Downhole Tool having Gas Breakout Assembly

Figure 1:
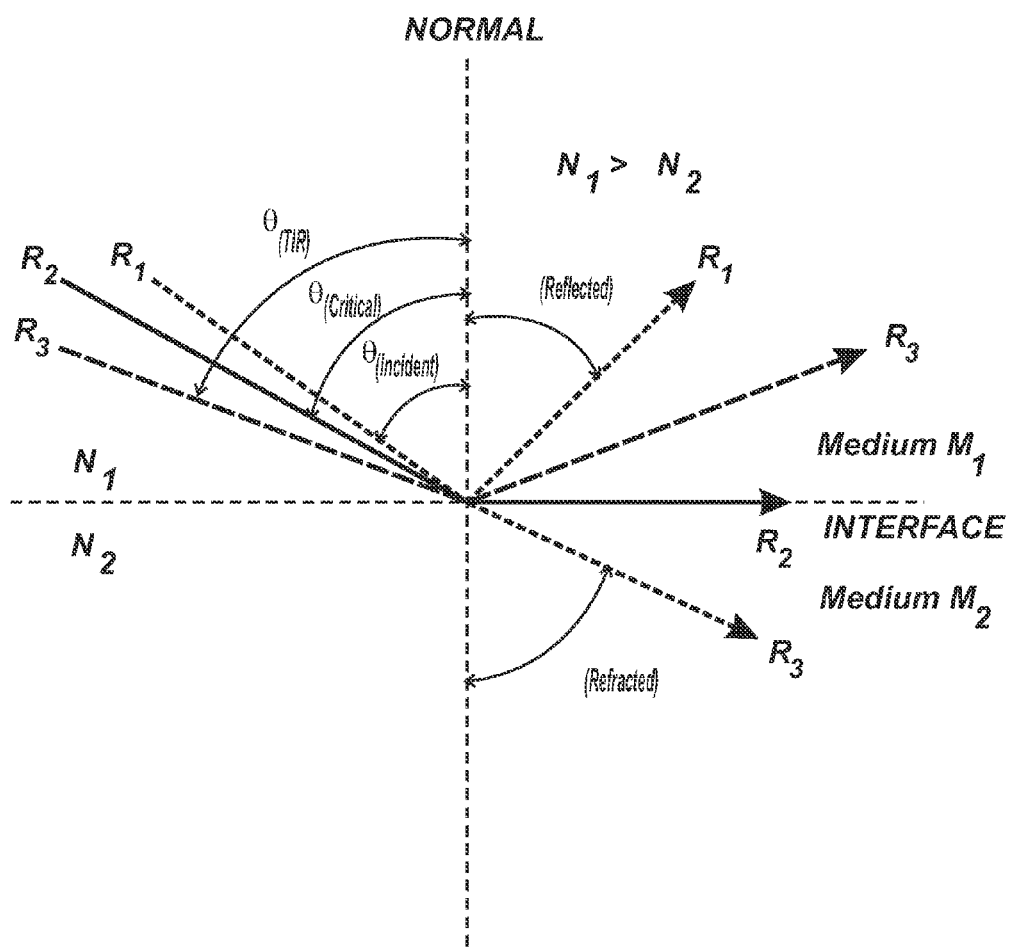
FIG. 1 illustrates light rays incident at different angles to an interface between two media with different refractive indices.
Figure 2:
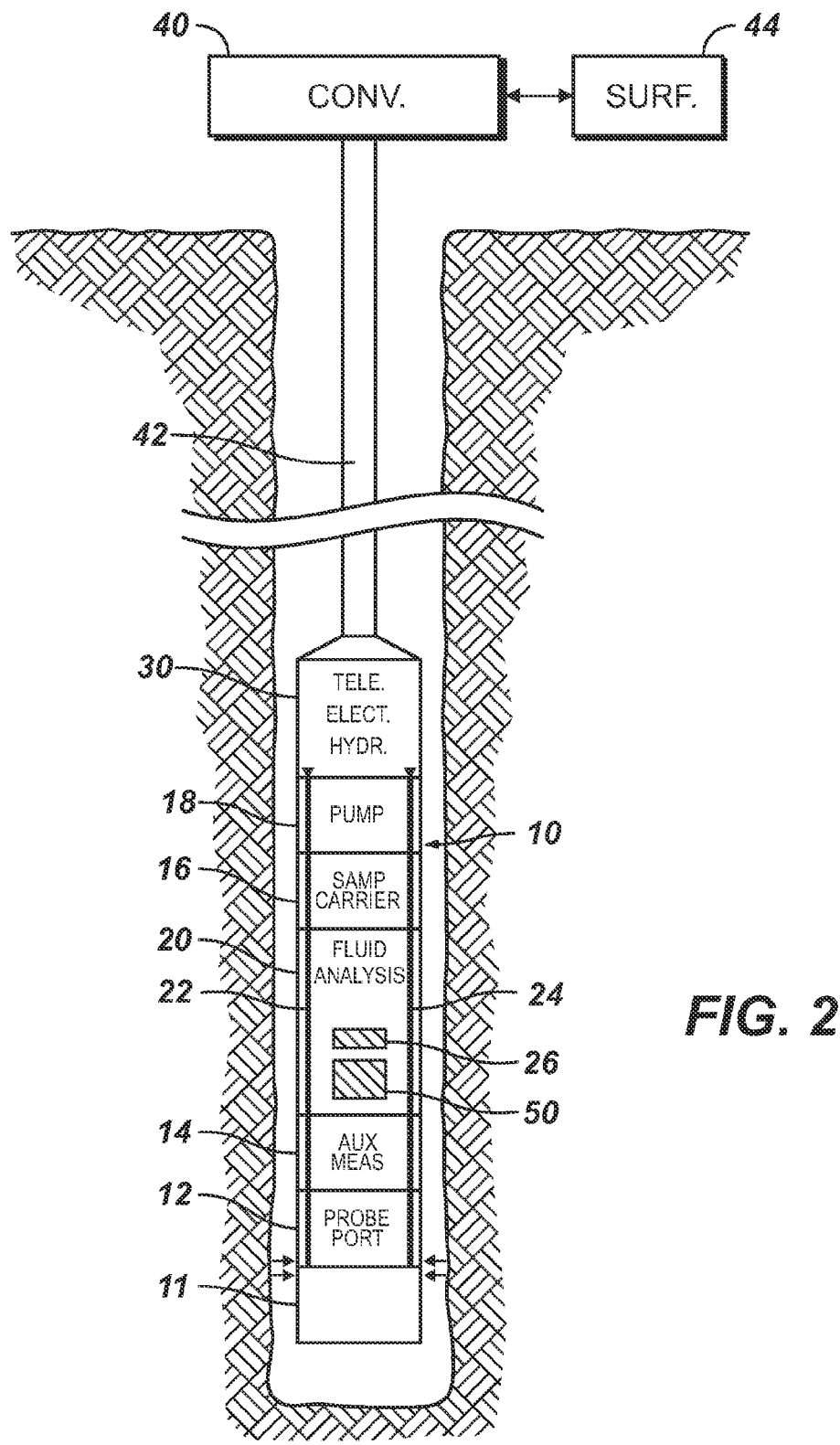
FIG. 2 conceptually illustrates a downhole tool disposed in a borehole environment of a well and having a gas breakout assembly of the present disclosure.

A downhole tool 10 shown in FIG. 2 operates in a borehole penetrating an earth formation. In one implementation, the downhole tool 10 is a formation tester, such as a wireline formation tester or drilling formation tester, and can be a formation tester such as disclosed in U.S. Pat. Pub. No. 2008/0173083, filed 24 Jan. 2007, which is incorporated herein by reference.

As shown, a conveyance apparatus 40 at the surface deploys the formation tester tool 10 downhole. For example, the tool 10 can be deployed using a tubular, a cable, a wireline, or similar component 42 or can be deployed during logging while drilling. Once deployed downhole, the tool 10 can be used to analyze fluids in the borehole environment. In general, the formation tester tool 10 can be conveyed along the borehole and can collect and analyze fluids from the formation to determine major constituents within the fluid either by stopping and pumping from an isolated zone in a borehole, by using production logging techniques known in the art, or by using some other available technique.

Typically, the formation tester tool 10 has a packer section 11, a probe or port section 12, a sample carrier section 16, a pump section 18, a fluid analysis section 20, and additional sections 30 for hydraulic, electronic, and downhole telemetry components. Dual fluid flow lines 22/24 extend through the tool 10 and are functionally configurable. However, other types of wireline or drilling formation tester tools could also be used, such as those having a single flow line.

In operation, the probe section 12 having an intake port draws fluid into the tool 10. To isolate the formation fluid samples from contaminates in the annulus, the tool 10 can use isolation elements, such as packers of section 11 or other devices, to isolate a region of the formation. The pump section 18 then pumps collected fluid from the probe section 12 into the tool 10 via the flow lines 22/24. The fluid, which can contain hydrocarbon components (solid, liquid, and/or gas) as well as drilling mud filtrate or other contaminants, flows through the tool 10, and various instruments and sensors in the tool 10 analyze the fluid. For example, the measurement section 14 can have sensors that measure various physical parameters (i.e., pressure, temperature, etc.) of the fluid.

The fluid analysis section 20 has a gas breakout assembly 50 according to the present disclosure optically coupled to at least one of the flow lines 22/24. The fluid analysis section 20 can also have other sensors for analyzing the fluid, including source and detector assemblies for downhole spectroscopy, for example. A processor 26 can be disposed in the fluid analysis section 20, although a processor located elsewhere in the formation tester tool 10 can alternatively be used to perform the fluid analysis. The sensors in the fluid analysis section 20 can determine physical and chemical properties of oil, water, and gas constituents of the downhole fluid sample passing through the flow line 22/24.

Eventually, fluid directed via the flow lines 22/24 either can be purged to the annulus or can be directed to the sample carrier section 16 where the samples can be retained for additional analysis at the surface. In section 30, hydraulic components can hydraulically operate valves and other elements within the tool 10, electronic components can provide control and power to various electronics, and telemetry components can communicate data via wireline or fluid telemetry to the surface. Uphole, surface equipment 44 can have a surface telemetry unit (not shown) to communicate with the downhole tool's telemetry components. The surface equipment 44 can also have a surface processor (not shown) that performs additional processing of the data measured by the tool 10.

It may be important that certain fluid properties remain within various limits for some sensors in the fluid analysis section 20 to operate properly or obtain useful data. For example, operation of the tool 10 can increase temperature and pressure of the sampled fluid in a way that can cause gas bubbles to form in the sample fluid. The breakout of gas in the sample fluid may then interfere with operation of some sensors or invalidate their results. Accordingly, the gas breakout assembly 50 detects the presence of such a gas breakout in the sample fluid, for example, when the tool 10 reduces the fluid's pressure below its bubble point. In general, gas breakout occurs at least when pressure of the downhole fluid falls below a bubble point of the fluid. Of course, the occurrence of gas breakout depends on other variables, the temperature, and constituents of the downhole fluid at the time.

To detect gas breakout, the gas breakout assembly 50 continuously monitors the fluid in at least one of the flow lines 22/24 and activates an alarm if gas breakout is detected. Based on the detected gas breakout, operation of the tool 10 may be altered so that the pressure is maintained above the bubble point as desired. Additionally, data from operation of other sensor units or detection of other fluid properties may or may not be taken as long as gas breakout is detected.

Although shown used in the formation tester tool 10, the gas breakout assembly 50 can be deployed in any suitable tool used for wireline formation testing, production logging, Logging While Drilling/Measurement While Drilling (LWD/MWD), or other operations. Therefore, the downhole tool 110 can be a wireline formation tester, a drilling formation tester, a production logging tool, or other temporary, permanent, or semi-permanent tool to take fluids from the borehole. In fact, the tool 110 can even deploy in a side pocket mandrel, for example, for a gas lift system or the like.

B. Gas Breakout Assembly

Figure 3:
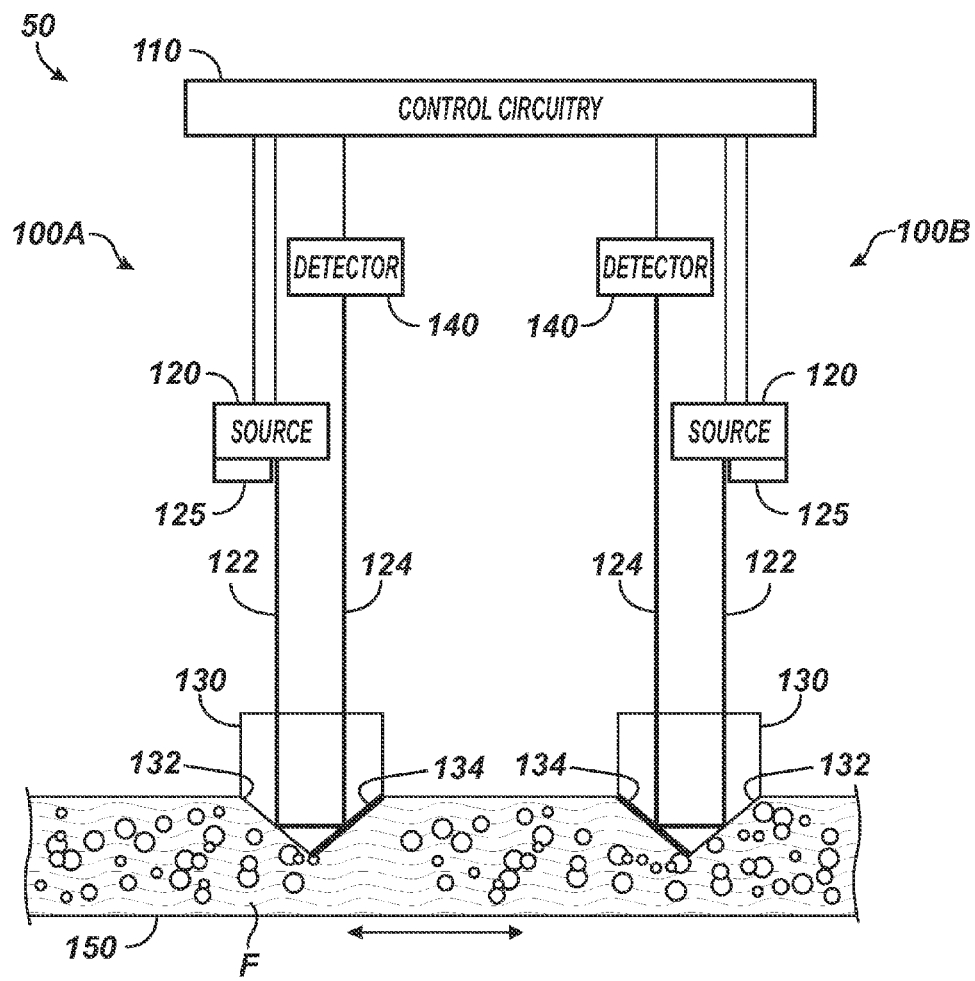
FIG. 3 illustrates a gas breakout assembly according to certain teachings of the present disclosure.

Given the above discussion of how the gas breakout assembly 50 can be used in a downhole tool, discussion now turns to FIG. 3. As shown, the gas breakout assembly 50 has dual gas breakout sensors 100A-B. Each sensor 100A-B has a source 120, a reference detector 125, a sensing optic 130, and a detector 140, and they can share control circuitry 110.

Use of the dual sensors 100A-B is preferred so that the assembly 50 can sense flow from either direction through a flow bus 150. For example, each sensor 100A-B can be identical to one another, but they can be situated in different directions relative to the flow bus 150. In this way, the assembly 50 can detect flow in either direction through the flow bus 150, as shown in FIG. 3. Alternatively, the sensors 100A-B can be identical, but can be situated in a similar direction relative to the flow bus 150. This may allow for redundancy.

In yet another alternative, the sensors 100A-B can have different configurations, such as different sources 120, different types of input signals (different polarizations, wavelengths, etc.), different materials for the sensing optics 130, different types of detectors 140, and/or different angular orientations, among other possible differences. This may give the gas breakout assembly 50 more versatility in sensing in downhole applications. Finally, although the assembly 50 has dual sensors 100A-B, it will be appreciated that the assembly 50 can in general have one or more such sensors 100, and these can share the same control circuitry 110 or have their own.

Figure 4A:
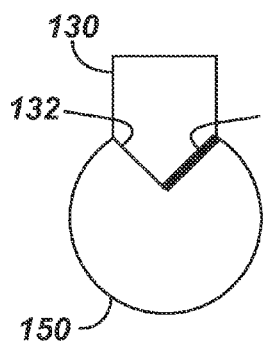
FIGS. 4A-4C shows different arrangements of a sensing optic in a flow passage.
Figure 4B:
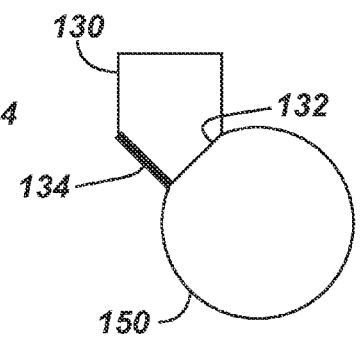
Figure 4C:
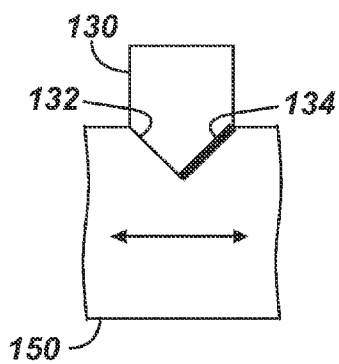

In general, the sensing optic 130 can be disposed in a number of ways relative to flow of fluid in the flow bus 150. For example, the sensing optic 130 in FIG. 4A fits in the flow bus 150 with both surfaces 132/134 in the flow. Alternatively, only the sensing surface 132 of the optic 130 in FIG. 4B is exposed to the flow bus 150. Finally, as shown in FIG. 4C, the sensing surface 132 can be exposed transversely to the flow of fluid in the flow bus 150. These and other alternate mounting configurations can be used.

Figure 5:
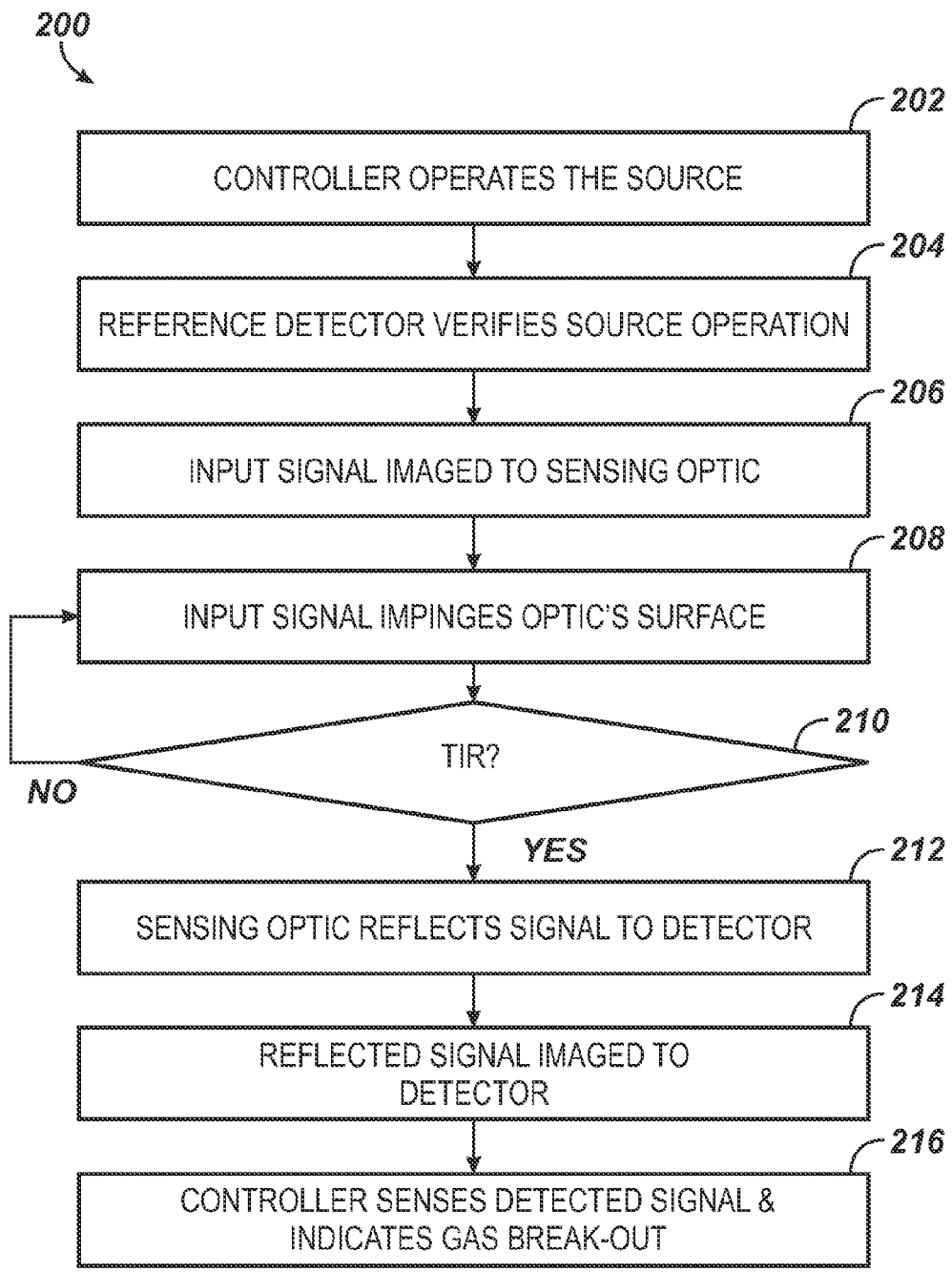
FIG. 5 shows an operating process of the gas breakout assembly.

During operation as shown in the process 200 of FIG. 5, the control circuitry 110 of FIG. 3 operates each sensor 100A-B as follows. The control circuitry 110 operates the source 120 to generate an input signal 122 (Block 202). Preferably, a reference detector 125 verifies whether the source 120 is operating or not (Block 204). A lens or other element focuses the input signal 122 and directs it into the sensing optic 130 (Block 206). At the optic 130, the signal 122 impinges the interface between the optic's sensing surface 132 and passing fluid in the flow bus 150 (Block 208).

The sensing optic 130 has a known refractive index, while the passing fluid F has an unknown refractive index, which varies depending on the composition and properties of the fluid F. If the refractive indices do not meet a defined relationship, then the input signal 122 impinging the interface will not be beyond the critical angle for the optic 130 and fluid F. Therefore, the signal 122 impinges the interface and refracts.

If the refractive indexes between the optic 130 and the fluid F meet the defined relationship, then the signal 122 impinging the interface will be impinging beyond the critical angle for the optic 130 and fluid F. In this instance, total internal reflectance occurs (Decision 210), and the signal 122 impinging the interface at the surface 132 reflects internally inside the sensing optic 130 (Block 212). The reflected signal 124 then reflects off the opposing mirrored surface 134 of the optic 130 and passes to the detector 140 (Block 214). (The mirrored surface 134 produces an internal mirror so its reflective surface faces towards the sensing optic 130.)

The control circuitry 110 monitors the intensity of the detector 140's response and determines that gas breakout has occurred in the fluid F flowing through the flow bus 150 if the response is above a certain threshold (Block 216). In particular, the control circuitry 110 senses a threshold measurement from the detector 140 and turns a gas flag "ON" or "OFF" based on the measurement. If either sensor 100A-B triggers the gas flag "ON," then the gas breakout assembly 50 indicates that gas breakout is occurring. However, when both detectors 140 have an optical signal response below a measurement threshold, then the gas flag remains "OFF." At this point, if gas break out is occurring, the control circuitry 110 alerts the operator that pressure in the flow bus 150 is below the bubble point of the fluid F so that corrective action can be taken.

As noted previously, the control circuitry 110 also monitors a reference detector 125, which can be a reference photodetector internal to the source 120. Because the source 120 is meant to remain "ON" during operation, the control circuitry 110 uses the reference detector 125 to confirm that the source 120 is operating. Otherwise, the source 120 may be "OFF," rendering the assembly's operation invalid. In this way, the reference detector 125 ensures that a false negative (e.g. no gas) in the gas breakout measurement does not occur because the source 120 is not actually operating when it is expected to be.

C. Details of Gas Breakout Sensor

Additional details of a gas breakout sensor are shown in FIG. 6. The source 120 generating the input signal can be a Light Emitting Diode (LED), a super-luminescent light emitting diodes (SLED), a laser diode (LD), or any light source that can be collimated. However, any continuous or pulsed broadband light source can be used with appropriate optical filtering. In addition, the source 120 can be a light emitting diode (LED) composed of multiple emitters with unique wavelengths, which could be operated independently or together. As noted previously, a reference photodiode (not shown) can be packaged into the LED source 120 to monitor the source 120's operation. Additionally, the input signal 122 generated by the source 120 may or may not be polarized, depending on the implementation.

As an LED, the source 120 preferably has a wavelength with minimal spectral absorption characteristics for the expected application. Because crude oil chemical compositions have a broad spectrum, there may be no particular wavelength that offers minimal absorption. In general, the LED source 120 can provide a wavelength from about 200 to 3000-nm. However, a wavelength of 850-nm from the LED source 120 may match a peak detection efficiency for high-temperature photodiodes that can be used for the detector 140.

In general, the change in center wavelength from the LED source 120 over the required thermal range may not significantly affect the detector's measurement response so that the LED source 120 may not need to be bandpass filtered. However, the input signal 122 from the source 120 can be shaped, filtered, and collimated using lenses, filters, apertures, and the like. For example, a collimator 126 collimates the input signal 122, and the collimated signal 122 passes through a slit 128 before entering a channel 61 in a housing block 60.

The input signal 122 enters the optic 130 and impinges the sensing surface 132 at an angle of incidence $\theta_1$ relative to the surface normal. If the refractive index of the fluid at the interface has a defined relationship to the optic 130's refractive index, then the angle of incidence $\theta_1$ for the input signal 122 will be beyond the critical angle. In this instance, the incident input signal 122 experiences total internal reflection and reflects off the interface at a reflected angle $\theta_r$. Traveling in the optic 130, the reflected signal 124 then impinges the mirrored surface 134 of the optic 130 at an angle $\theta_2$. The mirrored surface 134 can be a metal-mirrored surface preferably using Ni to withstand corrosion. Yet, any mirroring metal can be used with an appropriate protective overcoat.

The reflected signal 124 passes from the optic's mirrored surface 134, through the block's channel 61, and through a slit 148. Then, a lens 146 focuses the reflected signal onto the detector 140. In general, the detector 140 can be a single-element photodiode, a multi-element photodiode, an avalanche photodiode, a photomultiplier tube, a micro-channel plate, a bolometer, and/or a thermopile and can have any suitable detector material (e.g., Si, InGaAs, PbS, PbSe, MCT, etc.). However, as noted previously, the detector 140 is preferably a high-temperature photodiode. The detector 140 senses the intensity of the reflected signal 124. If the intensity is above a threshold indicative of total internal reflectance, then the sensor 100 turns "ON" and flags a gas breakout condition in the sample fluid of the flow line.

As noted previously, the gas breakout sensor 100 can determine whether the flow line's pressure is maintained above the fluid's bubble point. To do this, the gas breakout sensor 100 uses the principle of Total Internal Reflection (TIR) to sense the presence of gas in the flow line. As is known, Total Internal Reflection (TIR) is characterized by the difference in refractive indexes between two materials and how light can be reflected and/or refracted from the interface between those materials (Fresnel Equations and Snell's Law). As explained below, features of the gas breakout sensor 100 are designed based on these principles so that the sensor 100 turns "ON" (indicates gas breakout) when a predetermined relationship occurs between the refractive index of the sensor and that of the fluid.

In general, the sensing optic 130 can be made from a material having a refractive index at least greater than or equal to 1.65. In one embodiment, the sensing optic 130 is composed of sapphire with a nominal refractive index of 1.75. The downhole fluid can have water, brine, crude oil, liquefied hydrocarbons, gaseous hydrocarbons, and any combination of these and other fluids. Formation waters and brines typically have a refractive index ranging between 1.33 and 1.4, while crude oils typically have a refractive index ranging between 1.4 and 1.65. Liquefied gas typically has refractive index between 1.05 and 1.2 with the actual value depending on the composition. Gaseous formation hydrocarbons (i.e., methane, ethane, propane, etc.) have refractive indices of ~1.00.

With the sensor 100 operating in these conditions, the input signal 122 travels from the optic 130's high refractive index material (sapphire, $n_1 \approx 1.75$) to the fluid's lower refractive index $n_2$ (ranging from 1.00 for gases to ~1.6 for heavy crude oils). Consequently, according to Snell's Law, any angle of refraction in the fluid will be larger than the angle of incidence of the input signal 122 at the sensing surface 132. TIR occurs when this angle of incidence is larger than the critical angle $\theta_{crit}$, where the critical angle is characterized by:

$$\theta_{crit} = \arcsin\frac{n_2}{n_1}.$$

The sensor 100 turns a gas flag indication "ON" (i.e., the detector 140 detects a significant intensity of the reflected signal 124) when the fluid's (F) refractive index $n_2$ decreases such that the critical angle criteria is met and TIR occurs. Because the reduction in refractive index $n_2$ of the fluid occurs when the mixture has gaseous hydrocarbons, then a refractive index value $n_2$ below 1.2 (i.e. gaseous formation fluids and liquefied gas) provides an unambiguous indication of gas in the flow of fluid due to the sampled fluid's pressure being below its bubble point. Therefore, the gas flag of the sensor 100 is set to turn "ON" when the fluid's refractive index $n_2$ is approximately 1.2 with a transition range to about 1.3. The actual measurement is a signal intensity over threshold intensity value. Therefore, in practice, the actual refractive index $n_2$ at which the sensor 100 turns "ON" may be between 1.2 and 1.3.

Figure 10:
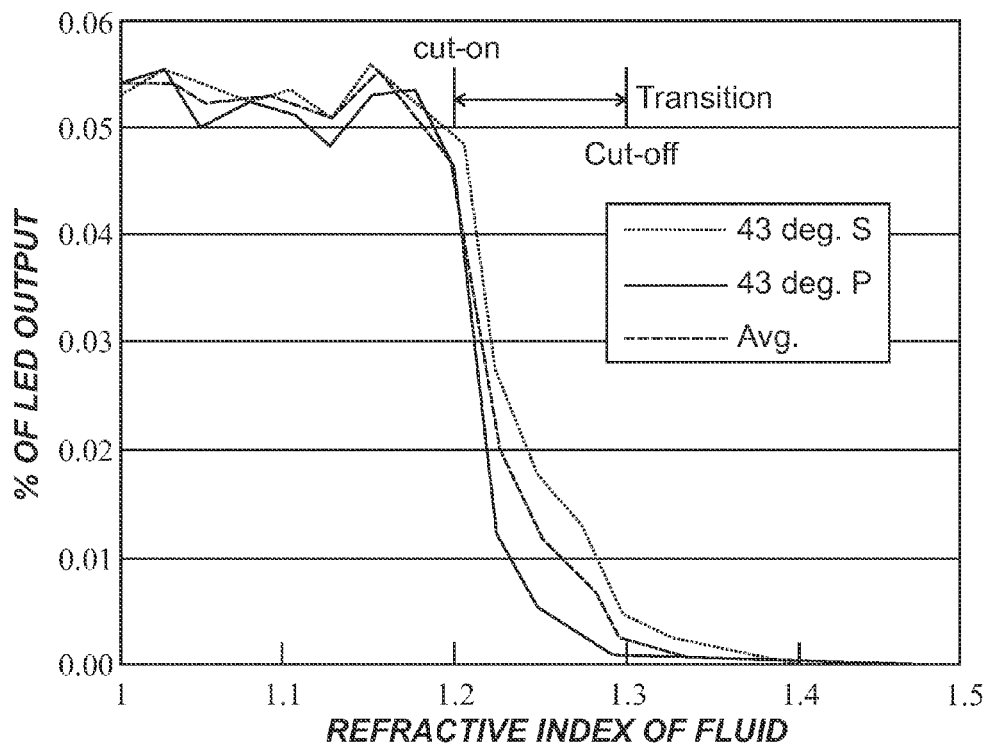
FIG. 10 graphs the detector's response of the source's intensity versus an estimate of the downhole fluid's refractive index.

For illustration, FIG. 10 graphs the estimated refractive index $n_2$ of sampled fluid relative to the detector's response, which is the measured intensity as a percentage of the source's output). During operation, an intermediate signal level may fall in the transition interval between 1.2 and 1.3 or 1.4. However, using a signal threshold comparison, the gas flag can be triggered "ON" at or near the value of 1.2. Therefore, the sensor 100 can indicate gas breakout when the detector's response exceeds a threshold (e.g., greater than some percentage of the source's output) that corresponds to the fluid's refractive index $n_2$ dropping below the threshold value of 1.2. Likewise, the gas flag can be triggered "OFF" when the detector's response falls below a threshold indicative of the fluid's refractive index $n_2$ being above about 1.3 or 1.4.

The predetermined relationship of the sensor can be defined by a number of variables. For example, different angles of the optic's surfaces, different light polarizations, the source's wavelength, and other variables can affect the expected signal response of the detector 140. These and other variables can be adjusted for a given implementation to improve the expected signal response depending on the circumstances.

As shown in FIG. 6, for example, the optic's surfaces 132/134 can have angles of α=47-degrees so that the angle of incidence $\theta_1$ at the sensing surface 132 is 43-degrees. (The mirrored surface 134 is oriented at a right angle to the sensing surface 132 so that the angle of incidence $\theta_2$ at this surface 134 is 47-degrees.) Making the angle of incidence at 132 be 42-degrees, 45-degrees, or some other value may alter the thresholds, which may be desirable for some implementations.

As noted previously, the measurement wavelength for the LED source 120 may be selected to be about 850-nm. The actual wavelength can vary depending on the implementation. Yet, any chosen wavelength may affect the angles on the sensing optic 130 because the wavelength used affects the critical angle.

In addition, a polarizer (not shown) can also be disposed in the collimated beam from the source 120 to select only P polarized light. This is expected to sharpen the transition from TIR to transmission as shown by the graphed response for P-polarized light in FIG. 10. Finally, the detector's signal response may be affected by thermal variations. To deal with such variations, the signal response for the detector 140 can be mapped against the response of the integrated reference detector (125; FIG. 3) so thermal variations can be accounted for.

D. Flow Bus having Sensor Units

With an understanding of the gas breakout assembly 50 and sensors 100, details of a particular implementation for a formation tester tool are shown in FIGS. 7A-7D. As shown in FIG. 7B, a housing 70 has sensor units 52/54 attached thereto. One sensor unit 52 can be a source assembly as disclosed in copending U.S. application Ser. No. 12/613,700, and the other sensor unit 54 can be a detector assembly as disclosed in copending U.S. application Ser. No. 12/613,808, which are incorporated herein by reference. These units 52/54 attached on opposing sides of the housing 70 to analyze fluid flowing through a flow passage 72.

The gas breakout sensors 100A-B of the assembly 50 also attach to the housing 70. As shown in FIG. 7A, the sensing optics 130 for both sensors 100A-B install with sealing elements 102 into optic apertures 74a-b defined in the housing 70. These apertures 74a-b position the sensing surfaces of the optics 130 into the flow passage 72 through the housing 70. The sealing elements 102 can include elastomeric high-pressure, high-temperature seals and other components to seal the optics 130 in the housing 70. However, other sealing methods known to those versed in the art can be used.

An optical retention block 60 affixes to the housing 70 and has channels 61 for communicating the input signal and reflected signal (if any) to and from the sensing optics 130. This retention block 60 also holds the optics 130 in place and provides a mechanical force to offset pressure in the flow passage 72.

A holder 62 and circuit board 64 attach to this retention block 60. The holder 62 can house the slits and collimators (not shown) described previously, and the circuit board 64 holds the LED sources (120) and detectors (140) described previously, as well as other necessary electronics to control the sources (120) and to interrogate the detectors (140). The detectors' signals can be communicated to an external controller to be manipulated (if desired). The detectors' signals can also be communicated to the tool string communication bus and ultimately to the surface using telemetry or the like.

As shown, a bubble director 80 installs in the flow passage 72 of the housing 70. This director 80 anchors at its end in the passage 72 (See FIG. 7D) and has a stem 82 with a plurality of vane sections 84a-c for routing the fluid flowing through the passage 72. As shown in the sectional views of FIG. 7D, the director 80 extends in the flow passage 72 relative to the sensing optics 130.

Details of the bubble director 80 are provided in FIGS. 8A-8C. The bubble director 80 has three vane sections 84a-c disposed along the stem 82. The end vane sections 84a/84c fit outside the sensing optics (130) in the flow passage (72), and the center vane section 84b fits between the two sensing optics (130) (See FIG. 7D). In this way, the bubble director 80 can direct the flow through the passage 72 in either direction, and representative formation fluid can reach at least one sensing surface (132) regardless of the tool's orientation.

Each vane section 84a-c has two spiral-shaped vanes 85. These vanes 85 are offset on opposite sides of the stem 82, and each twists clockwise about 180-degrees around the axis of the stem 82. As they spiral, the vanes 85 increase in diameter from the stem 82 to a maximum diameter before decreasing to the diameter of the stem 82 again. The maximum diameter of the vanes 85 is preferably equal to the diameter of the flow passage 72. For its part, the diameter of the stem 82 is naturally less than the diameter of the flow passage 72. In one implementation, for example, the stem 82 may have a diameter that is almost ⅓ of the diameter for the flow passage 72.

The anchor 86 attached on one end of the stem 82 anchors onto the open end of the flow passage 72 using a fastener or the like (not shown). As shown, the anchor 86 preferably includes a tab 88 that fits into a slot of the fastener or flow passage 72 to prevent the director 80 from rotating due to flow. Other techniques could be used to anchor the stem 82 in the flow passage 72. Preferably, the ends of the stem 82 as well as any interconnecting struts for the anchor 86 and other surfaces of the director 80 are curved and rounded to accommodate the flow of fluid.

Although flow routing may not actually be required for operation, the bubble director 80 is intended to optimize downhole performance. If the gas breakout assembly 50 fails to recognize that gas is present in the flow, for example, then the assembly 50 will fail to detect any change in the flow to below the bubble point even if gas bubbles are actually present in the fluid. Therefore, the presence of gas bubbles may be missed without the bubble director 80, and any current reading from the gas breakout assembly 50 would not be an accurate gas flag measurement. As will be appreciated, an inaccurate gas flag measurement can affect subsequent determinations of the reserves available downhole.

For these reasons, the bubble director 80 helps transport or route any bubbles present in the flow to at least one of the sensing optics 130 for detection of the gas bubbles regardless of the direction of the flow. When installed in the flow passage 72 as shown in FIG. 7D, the director 80 rotates the flow in the passage 72. Because the sensing surface 134 exposed in the passage 72 is oriented to the side of the passage, the spiral-shaped vanes 85 with their clockwise twist may tend to wash the flow and bubbles past the sensing surface 134 at an angle relative to the axis of the stem 82.

The spacing and length of the vane sections 84a-c is intended to increase the rotation of the flow through the flow passage 72 and can be configured for a given implementation. More or less vane sections 84a-c can be provided if more or less sensing optics (130) are used or if increased fluid movement is required. As an alternative to separate vane sections 84a-c, an entire length of the stem 82 may have vanes 85 spiraling thereon in several turns. In fact, the vanes 85 may even pass the location of where the sensing optics (130) are exposed in the flow passage 72.

The flow routing provided by the bubble director 80 helps bring representative formation fluid samples to the sensing surfaces (132) of the sensing optics 130 and directs bubbles in the flow to strike the sensing optics 130 in particular areas that facilitate gas bubble detection. Having the spiral design, the vane sections 84 help ensure that bubbles in the flow are not missed due to gravity or other reasons as they are transported through the flow passage 72. All the same, the director 80 preferably maintains the flow rate of the fluid from the formation unchanged and preferably avoids trapping and building mudcake in the tool's flow passage 72.

Figure 9A:
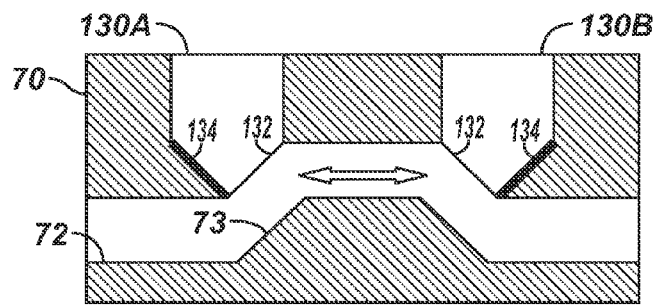
FIGS. 9A-9B show alternate arrangements of sensing optics and flow passages.
Figure 9B:
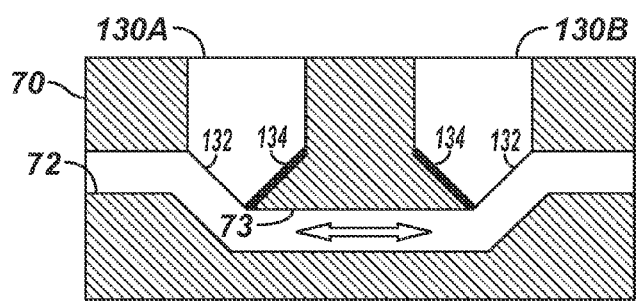

Alternate arrangements of sensing optics and passages are shown in FIG. 9A-9B. In these arrangements, the sensing surfaces 132 of the optics 130A-B are positioned transverse to the flow passage 72 and flow. In FIG. 9A, the sensing surfaces 132 face inward toward one another, and a mixing contour 73 in the flow passage 72 helps mix the flow and bring the fluid to the sensing surfaces 132. As noted, this contour 73 can bring bubbles to the sensing surfaces 132. In FIG. 9B, the sensing surfaces 132 face outward from one another and away from the mixing contour 73. The alternately facing surfaces 132 enable the optics 130 to monitor flow in either direction through the flow passage 72.

Although this disclosure refers to electromagnetic radiation using the terms "signal," "light," "emission," and the like, these references are actually intended to include wavelengths outside the bounds of visible light. Further, while the discussion herein may have focused on a particular wavelength, it will be appreciated that the disclosed sensor 100 can be configured to handle any suitable wavelength of electromagnetic radiation, including wavelengths in the ultraviolet, visible, near infrared, and infrared regions of the electromagnetic spectrum.

The foregoing description of preferred and other embodiments is not intended to limit or restrict the scope or applicability of the inventive concepts conceived of by the Applicants. It should be understood that the sensor 100 can use various types of sensing optic shapes, lens systems, sources, and detectors depending upon the dynamic range requirements of the sensor 100 and the physical dimensions of the sensor 10 dictated by packing requirements.

In exchange for disclosing the inventive concepts contained herein, the Applicants desire all patent rights afforded by the appended claims. Therefore, it is intended that the appended claims include all modifications and alterations to the full extent that they come within the scope of the following claims or the equivalents thereof.

What is claimed is:

1. A downhole gas breakout sensor for a downhole tool having a flow passage for downhole fluid, the downhole fluid having a variable refractive index, the sensor comprising:
    a first source generating a first input signal;
    a first sensing optic having a first refractive index and having a first surface, the first surface optically coupled to the first source and interfacing with the downhole fluid having the variable refractive index in the flow passage;
    a bubble director disposed in the flow passage and directing the downhole fluid flowing in the flow passage; and
    a first measurement detector optically coupled to the first sensing optic and detecting a first reflected signal from the first surface, the detection of the first reflected signal resulting from a first defined relationship between the first refractive index and the variable refractive index and being indicative of gas breakout in the downhole fluid.

2. The sensor of claim 1, wherein the first source comprises a light emitting diode (LED), a light emitting diode (LED) composed of multiple emitters with unique wavelengths, a super-luminescent light emitting diodes (SLED), a laser diode (LD), or a broadband source.

3. The sensor of claim 1, wherein the first sensing optic comprises a second surface being reflective and reflecting the reflected signal from the first surface to the first measurement detector.

4. The sensor of claim 1, wherein the first input signal has a wavelength between 200 and 3000 nm.

5. The sensor of claim 1, wherein the first sensing optic comprises a material selected from the group consisting of sapphire, ruby, zircon, cubic zirconium, diamond, garnet, and a material having an index of refraction at least greater than or equal to 1.65.

6. The sensor of claim 1, wherein the gas breakout is indicated at least when pressure of the downhole fluid falls below a bubble point of the downhole fluid.

7. The sensor of claim 1, wherein the first defined relationship produces total internal reflection in the first sensing optic.

8. The sensor of claim 7, wherein the total internal reflection occurs when the variable refractive index of the fluid is approximately 1.2.

9. The sensor of claim 1, further comprising a reference detector optically coupled to the first source and detecting the first input signal from the first source.

10. The sensor of claim 9, wherein failure to detect the first reflected signal with the first measurement detector is ignored if the reference detector fails to detect the first input signal.

11. The sensor of claim 1, wherein the first measurement detector is selected from the group consisting of a single-element photodiode, a multi-element photodiode, an avalanche photodiode, a photomultiplier tube, a micro-channel plate, a bolometer, and a thermopile.

12. The sensor of claim 1, further comprising control circuitry operatively coupled to the first source and the first measurement detector.

13. The sensor of claim 12, wherein the control circuitry determines the gas breakout in the fluid when the first measurement detector senses an intensity of the first reflected signal from the first surface of the first sensing optic above a threshold.

14. The sensor of claim 12, further comprising a reference detector optically coupled to the first source and detecting the first input signal from the first source, the control circuitry operatively coupled to the reference detector and determining whether the reference detector fails to detect the first input signal.

15. The sensor of claim 1, further comprising a housing having a the flow passage and holding the first sensing optic relative to the flow passage.

16. The sensor of claim 1, wherein the bubble director comprises a stem having vanes disposed along an axis of the stem.

17. The sensor of claim 16, wherein the vanes spiral along the axis of the stem.

18. The sensor of claim 16, wherein a first section of the vanes is disposed on the stem at a first location on one side of the sensing optic, and wherein a second section of the vanes is disposed on the stem at a second location on an opposite side of the sensing optic.

19. The sensor of claim 1, wherein the bubble director comprises a contour defined in the flow passage.

20. The sensor of claim 1, further comprising:
a second source generating a second input signal;
a second sensing optic having a second refractive index and having a second surface, the second surface optically coupled to the second source and interfacing with the downhole fluid having the variable refractive index; and
a second measurement detector optically coupled to the second sensing optic and detecting a second reflected signal from the second surface, the detection of the second reflected signal resulting from a second defined relationship between the second refractive index and the variable refractive index and being indicative of gas breakout in the downhole fluid.

21. The sensor of claim 20, wherein the first and second sensing surfaces face in opposite directions.

22. The sensor of claim 20, wherein the second source has a wavelength different than the first source, and wherein the second sensing optic, the second refractive index, and the second measurement detector are each similar to the first sensing optic, the first refractive index, and the first measurement detector.

23. The sensor of claim 20, wherein the second source, the second sensing optic, the second refractive index, and the second measurement detector are each similar to the first source, the first sensing optic, the first refractive index, and the first measurement detector.

24. The sensor of claim 1, further comprising a tool deployable downhole and having a tool housing, the tool housing having the flow passage for the downhole fluid and having the downhole gas breakout sensor disposed therein relative to the flow passage.

25. A downhole fluid analysis tool for downhole fluid having a variable refractive index, the tool comprising:
a tool housing deployable downhole and having a flow passage for the downhole fluid,
a bubble director disposed in the flow passage and directing the downhole fluid flowing in the flow passage; and
a fluid analysis device disposed in the tool housing relative to the flow passage, the fluid analysis device at least including:
a first source generating a first input signal;
a first sensing optic having a first refractive index and having a first surface, the first surface optically coupled to the first source and interfacing with the downhole fluid having the variable refractive index; and
a first measurement detector optically coupled to the first sensing optic and detecting a first reflected signal from the first surface, the detection of the first reflected signal resulting from a first defined relationship between the first refractive index and the variable refractive index and being indicative of gas breakout in the downhole fluid.

26. The tool of claim 25, wherein the tool alters flow of the downhole fluid in the flow passage in response to the fluid analysis device.

27. The tool of claim 25, wherein the bubble director comprises a stem having vanes disposed along an axis of the stem.

28. The tool of claim 27, wherein the vanes spiral along the axis of the stem.

29. The tool of claim 27, wherein a first section of the vanes is disposed on the stem at a first location on one side of the sensing optic, and wherein a second section of the vanes is disposed on the stem at a second location on an opposite side of the sensing optic.

30. The tool of claim 25, wherein the bubble director comprises a contour defined in the flow passage.

31. A downhole fluid analysis method for downhole fluid in a flow passage of a downhole tool, the downhole fluid having a variable refractive index, the method comprising:
generating a first input signal;
directing the input signal into a sensing optic;
interacting the first input signal in the first sensing optic with a first interface between the first sensing optic and the downhole fluid in the flow passage, the first sensing optic have a first refractive index, the variable refractive index of the downhole fluid being variable relative to the first refractive index;
directing any bubbles in the downhole fluid relative to the first sensing optic by directing the downhole fluid flowing in the flow passage with a bubble director disposed in the flow passage; and detecting a first reflected signal from the first interface indicative of gas breakout in the downhole fluid.

32. The method of claim 31, further comprising:
initially deploying the downhole tool downhole; and
analyzing the downhole fluid by performing the steps of generating the first input signal, directing the first input signal, interfacing the first input sign, directing any bubbles, and detecting the first reflected signal.

33. The method of claim 31, wherein generating the first input signal comprises operating a source comprising a light emitting diode (LED), a light emitting diode (LED) composed of multiple emitters with unique wavelengths, a super-luminescent light emitting diodes(SLED), a laser diode (LD), or a broadband source.

34. The method of claim 31, wherein generating the first input signal comprises generating the first input signal with a wavelength between 200 and 3000 nm.

35. The method of claim 31, wherein the first sensing optic comprises a material selected from the group consisting of sapphire, ruby, zircon, cubic zirconium, diamond, a garnet, and a material having an index of refraction at least greater than or equal to 1.65.

36. The method of claim 31, wherein the gas breakout is indicated at least when pressure of the downhole fluid falls below a bubble point of the downhole fluid.

37. The method of claim 31, wherein detecting the first reflected signal comprises arranging the detection of the first reflected signal based on a first defined relationship between the first refractive index and the variable refractive index and being indicative of the gas breakout in the downhole fluid.

38. The method of claim 37, wherein the first defined relationship corresponds to a total internal reflection occurring in the first sensing optic.

39. The method of claim 37, wherein the first defined relationship corresponds to a total internal reflection occurring in the first sensing optic.

40. The method of claim 31, further comprising detecting the first input signal directly as a reference signal.

41. The method of claim 40, further comprising ignoring a failure to detect the first reflected signal if the reference signal is not detected.

42. The method of claim 31, further comprising determining the gas breakout in the downhole fluid when sensing an intensity of the first reflected signal above a threshold.

43. The method of claim 31, wherein directing the downhole fluid flowing in the flow passage with the bubble director disposed in the flow passage comprises directing the downhole fluid with vanes disposed along an axis in the flow passage.

44. The method of claim 43, wherein directing the downhole fluid with the vanes disposed along the axis in the flow passage comprises spiraling the downhole fluid with the vanes along the axis.

45. The method of claim 31, wherein directing the downhole fluid flowing in the flow passage with the bubble director disposed in the flow passage comprises directing the downhole fluid flowing in the flow passage on opposite sides of the interface with the sensing optic.

46. The method of claim 31, wherein directing the downhole fluid flowing in the flow passage with the bubble director disposed in the flow passage comprises directing the downhole fluid with a contour defined in the flow passage.

47. The method of claim 31, further comprising:
generating a second input signal;
directing the second input signal into a second sensing optic;
interfacing the second input signal in the second sensing optic with a second interface between the second sensing optic and the downhole fluid in the flow passage, the second sensing optic have a second refractive index, the variable refractive index of the downhole fluid being variable relative to the second refractive index; and
detecting a second reflected signal from the second interface indicative of gas breakout in the downhole fluid.

48. The method of claim 47, wherein the second input signal, the second sensing optic, and the second refractive index are each similar to the first input signal, the first sensing optic, and the first refractive index.

49. The method of claim 47, wherein the first and second interfaces face in opposite directions.

50. The method of claim 47, wherein the second input signal has a wavelength different than the first input signal, and wherein the second sensing optic and the second refractive index are similar to the first sensing optic and the first refractive index.

51. A downhole fluid analysis method for downhole fluid, the downhole fluid having a second refractive index, the method comprising:
deploying a tool downhole, the tool having a flow passage for the downhole fluid; and
analyzing the downhole fluid by:
generating an input signal;
directing the input signal into a sensing optic;
interacting the input signal in the sensing optic with an interface between the sensing optic and the downhole fluid in the flow passage, the sensing optic have a first refractive index, the second refractive index of the downhole fluid being variable relative to the first refractive index;
directing any bubbles in the downhole fluid relative to the sensing optic by directing the downhole fluid flowing in the flow passage with a bubble director disposed in the flow passage; and
detecting a reflected signal from the interface indicative of gas breakout in the downhole fluid.

52. The method of claim 51, wherein directing the downhole fluid flowing in the flow passage with the bubble director disposed in the flow passage comprises directing the downhole fluid with vanes disposed along an axis in the flow passage.

53. The method of claim 52, wherein directing the downhole fluid with the vanes disposed along the axis in the flow passage comprises spiraling the downhole fluid with the vanes along the axis.

54. The method of claim 51, wherein directing the downhole fluid flowing in the flow passage with the bubble director disposed in the flow passage comprises directing the downhole fluid flowing in the flow passage on opposite sides of the first sensing optic.

55. The method of claim 51, wherein directing the downhole fluid flowing in the flow passage with the bubble director disposed in the flow passage comprises directing the downhole fluid with a contour defined in the flow passage.

* * * * *